(12) United States Patent
Wu (10) Patent No.: US 8,826,464 B2
(45) Date of Patent: Sep. 9, 2014

(54) FILTER HOLDING SYSTEM FOR WELDING MASK

(75) Inventor: Ziqian Wu, NanJing (CN)

(73) Assignee: Tecmen Electronics Co., Ltd., Nanjing (CN)

( * ) Notice: Subject to any disclaimer, the term of this patent is extended or adjusted under 35 U.S.C. 154(b) by 412 days.

(21) Appl. No.: 13/248,828

(22) Filed: Sep. 29, 2011

(65) Prior Publication Data

US 2013/0081190 A1 Apr. 4, 2013

(51) Int. Cl.
*A42B 1/00* (2006.01)
*A61F 9/06* (2006.01)
*G02B 7/00* (2006.01)

(52) U.S. Cl.
CPC .. *A61F 9/06* (2013.01); *G02B 7/006* (2013.01)
USPC .............................................................. 2/8.2

(58) Field of Classification Search
USPC ........................ 2/7–9, 8.2–8.5, 8.7, 8.8, 424
See application file for complete search history.

(56) References Cited

U.S. PATENT DOCUMENTS

| | | | |
|---|---|---|---|
| 5,571,217 A | 11/1996 | Del Bon et al. | |
| D394,732 S | 5/1998 | Huh | |
| D398,421 S | 9/1998 | Crafoord et al. | |
| 5,857,215 A | 1/1999 | Fergason et al. | |
| 6,134,716 A * | 10/2000 | Richardson | 2/202 |
| 6,151,711 A * | 11/2000 | Edwards | 2/8.3 |
| 6,185,739 B1 | 2/2001 | Verkic et al. | |
| 6,230,328 B1 | 5/2001 | Holloway | |
| D444,919 S | 7/2001 | Kramer et al. | |
| 6,401,244 B1 * | 6/2002 | Kramer et al. | 2/8.1 |
| D481,832 S | 11/2003 | Huh | |
| D482,502 S | 11/2003 | Huh | |
| D499,215 S | 11/2004 | Cheng | |
| 6,938,276 B1 * | 9/2005 | Prendergast | 2/422 |
| D521,190 S | 5/2006 | Wu | |
| D524,991 S | 7/2006 | Martin et al. | |

(Continued)

FOREIGN PATENT DOCUMENTS

| | | |
|---|---|---|
| CN | 201542816 U | 8/2010 |
| CN | 201759738 U | 3/2011 |

OTHER PUBLICATIONS

International Bureau of WIPO, International Search Report in International Patent Application No. PCT/CN2012/081923 (Jan. 3, 2013).

(Continued)

*Primary Examiner* — Katherine Moran
(74) *Attorney, Agent, or Firm* — Leydig, Voit & Mayer, Ltd.

(57) ABSTRACT

A filter holding system for holding an optical filter to a mask casing of a welding mask. The filter holding system can include a holding frame body configured for supporting and accommodating the optical filter, and a connecting mechanism which is provided on the holding frame body and is configured for connecting or disconnecting the holding frame body to or from the mask casing. The connecting mechanism can have a disconnect position and a connect position. In the disconnect position, the connecting mechanism disconnects the holding frame body from the mask casing, and in the connect position, the connecting mechanism connects the holding frame body and the mask casing. A welding mask can comprise a mask casing, a headgear, a protective film, an optical filter and a filter holding system.

15 Claims, 9 Drawing Sheets

(56) References Cited

U.S. PATENT DOCUMENTS

| | | |
|---|---|---|
| D527,849 S | 9/2006 | Huh |
| D530,864 S | 10/2006 | Huh |
| D540,989 S | 4/2007 | Huh |
| D540,990 S | 4/2007 | Huh |
| 7,308,719 B2 | 12/2007 | Huh |
| D565,800 S | 4/2008 | Wang |
| D565,801 S | 4/2008 | Curci et al. |
| 7,409,723 B2 | 8/2008 | Huh |
| D584,006 S | 12/2008 | Juhlin |
| D584,858 S | 1/2009 | Wang |
| D586,956 S | 2/2009 | Huh |
| D594,600 S | 6/2009 | Huh |
| D628,750 S | 12/2010 | Schwanz |
| D635,721 S | 4/2011 | Cheng |
| D636,129 S | 4/2011 | Wu |
| D637,353 S | 5/2011 | Wang |
| D640,419 S | 6/2011 | Wright |
| 2007/0079417 A1 | 4/2007 | Huh |
| 2008/0060102 A1 | 3/2008 | Matthews et al. |
| 2010/0287676 A1 | 11/2010 | Seo |
| 2011/0119801 A1 | 5/2011 | Wright |

OTHER PUBLICATIONS

International Bureau of WIPO, Written Opinion in International Patent Application No. PCT/CN2012/081923 (Jan. 3, 2013).

International Bureau of WIPO, International Preliminary Report on Patentability in International Patent Application No. PCT/CN2012/081923 (Apr. 1, 2014).

\* cited by examiner

FILTER HOLDING SYSTEM FOR WELDING MASK

FIELD

The technical field relates to a filter holding system for a welding mask.

BACKGROUND

During welding operation, an operator is required to wear a welding mask to prevent harm to the operator's body caused by spatters and various harmful rays generated in welding. Current welding masks generally comprise a mask casing, a headgear, a protective film and an optical filter. The protective film and the optical filter are fixed to the mask casing, for example, by means of bolts, screws and even rivets. The protective film needs to be occasionally replaced because it is in contact with the spatters and can be damaged during welding operation. Meanwhile, the optical filter also needs to be changed when necessary in order to adapt to different welding conditions. The fixed connection between the protective film, the optical filter, and the mask makes it difficult to change the protective film and the optical filter.

SUMMARY

An improvement to the connection mechanism is described to make the replacement of the protective film and the optical filter easier while maintaining the reliability of the connection.

To this end, a holding system for holding an optical filter to a mask casing of a welding mask is described.

According to an embodiment, the holding system comprises a holding frame body configured for supporting and accommodating the optical filter, and a connecting mechanism which is provided on the holding frame body and is configured for connecting or disconnecting the holding frame body to or from the mask casing. The connecting mechanism has a disconnect position and a connect position. In the disconnect position, the connecting mechanism disconnects the holding frame body from the mask casing, so that the holding frame body and the mask casing are separated from each other; and in the connect position, the connecting mechanism connects the holding frame body and the mask casing, so that the holding frame body is connected to the mask casing.

In an embodiment, the connecting mechanism comprises a connecting pin, a driving block and a manipulating unit. In a disconnected position, the connecting pin is completely accommodated in a connecting pin accommodating cavity of the holding frame body, and in a connected position, the connecting pin extends out of a lateral opening of the connecting pin accommodating cavity and is inserted into an accommodating cavity of the mask casing. The driving block connects the connecting pin and the manipulating unit, so that the connecting pin is configured to be moved with the manipulating unit, and thereby, the holding system is switched between the disconnect position and the connect position.

In an embodiment, a plurality of rails are provided on a side wall of the connecting pin accommodating cavity, and the manipulating unit is placed on the holding frame body in a manner of sliding along the rails.

In an embodiment, a plurality of stop protrusions are provided on each of the rails, and a plurality of corresponding stop protrusions are provided on the manipulating unit. The manipulating unit is configured to be positioned in the disconnect position and in the connect position by means of the mating of these stop protrusions, wherein the manipulating unit is switched between the disconnect position and the connect position under a sufficient external force.

In an embodiment, on a bottom wall of the holding frame body there are two connecting mechanisms, and on a top wall of the holding frame body there are one or more protrusions. The protrusions can pass through one or more through holes provided on the mask casing so that the holding system can be connected on the mask casing with the cooperation between the connecting mechanisms and the protrusion(s) on the top wall of the holding frame body.

In an embodiment, each of the bottom wall and the top wall of the holding frame body is provided with two connecting mechanisms.

In an embodiment, an outer surface of the manipulating unit is roughened, which facilitates an operator to move the manipulating unit leftwards or rightwards.

In an embodiment, the holding system is made of synthetic fiber, such as nylon.

In an embodiment, the connecting pin accommodating cavity and the connecting pin can have any suitable cross-sectional shape, such as rectangular, square, or pie-shaped.

In another embodiment, the welding mask has a mask casing, a protective film, a headgear, an optical filter and a filter holding system, wherein the optical filter is held in the filter holding system and is connected on the welding mask together with the protective film by means of the filter holding system.

By means of the holding system described herein, holding the protective film and the filter onto the mask casing can be achieved through the following steps:

First, placing the protective film in the frame accommodating portion on the mask casing;

Next, fixing the filter on the holding frame body, and then placing the holding system with the optical filter in the frame accommodating portion on the mask casing; and Finally, moving the manipulating unit of the holding system to insert the connecting pin of the holding system into a corresponding accommodating cavity provided on the mask casing, which results in the protective film and the filter being maintained on the mask casing simultaneously.

Accordingly, the following advantages can be achieved: 1. the filter can be held on the mask casing or can be removed from the mask casing by a welding operator moving the manipulating unit of the filter holding system without using any tools; and 2. at the same time as the filter is held on the mask casing or is removed from the mask casing, the protective film is also held on the mask casing or is also removed from the mask casing by means of the filter holding system described herein, which, in particular, facilitates changing the protective film when necessary.

BRIEF DESCRIPTION OF THE DRAWINGS

The filter holding system will be described in more detail in connection with the attached drawings, in which.

The same components or components with the same functions are denoted by the same reference numerals.

DETAILED DESCRIPTION

The filter holding system is further described in detail below by way of an illustrated embodiment, which will be described with reference to the drawings.

Figure 1:
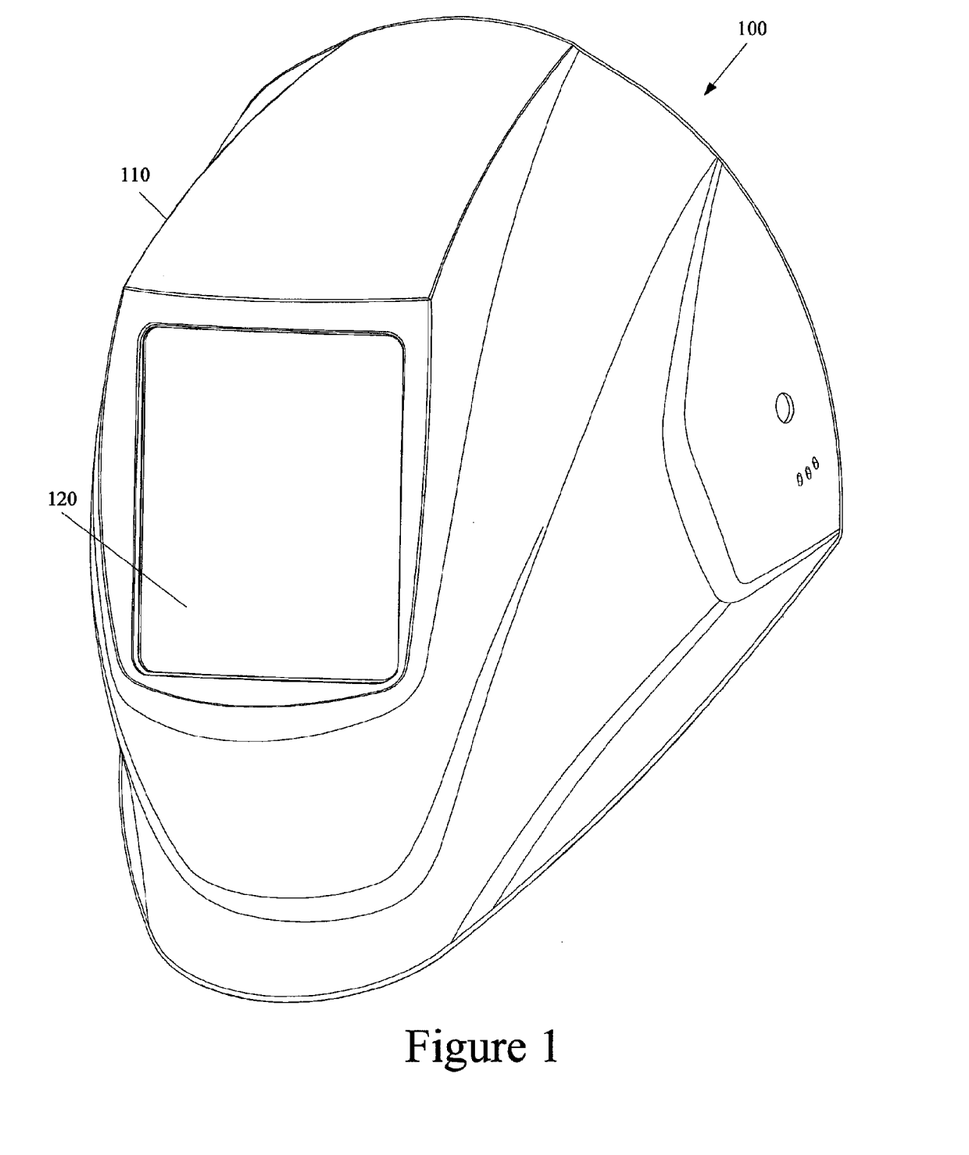
FIG. 1 is a perspective view of a welding mask.

With reference to FIG. 1, a welding mask 100 generally comprises a mask casing 110 and an observing window 120. The mask casing 110 is mainly used to shield splashed welding materials during welding operation. In addition, the mask casing 110 is also used for supporting and fixing the observing window 120. The observing window 120 is mainly used to protect the eyes of a welding operator from being harmed by spatters and various harmful rays during the welding operation.

The mask casing 110 can be, for example, made of synthetic fiber, such as nylon. The shape of the mask casing 110 is configured to follow the profile of the head of a welding operator. The mask casing 110 can have accessories for improving comfort and stability of the welding mask 100 when a welding operator is wearing the welding mask 100. Said accessories can be, for example, cushions (such as a sponge cushion), which are provided inside of the mask casing and can be made of an elastic material. Said accessories also can be, for example, one or more headgears having ends fixed to the mask casing and a main body which can be placed around the chin or behind the head of an operator, so that the mask casing 110 is reliably secured to the operator's head. Preferably, the length of the headgear is adjustable, so that the mask casing 110 can be worn by operators with different head profiles.

Figure 2:
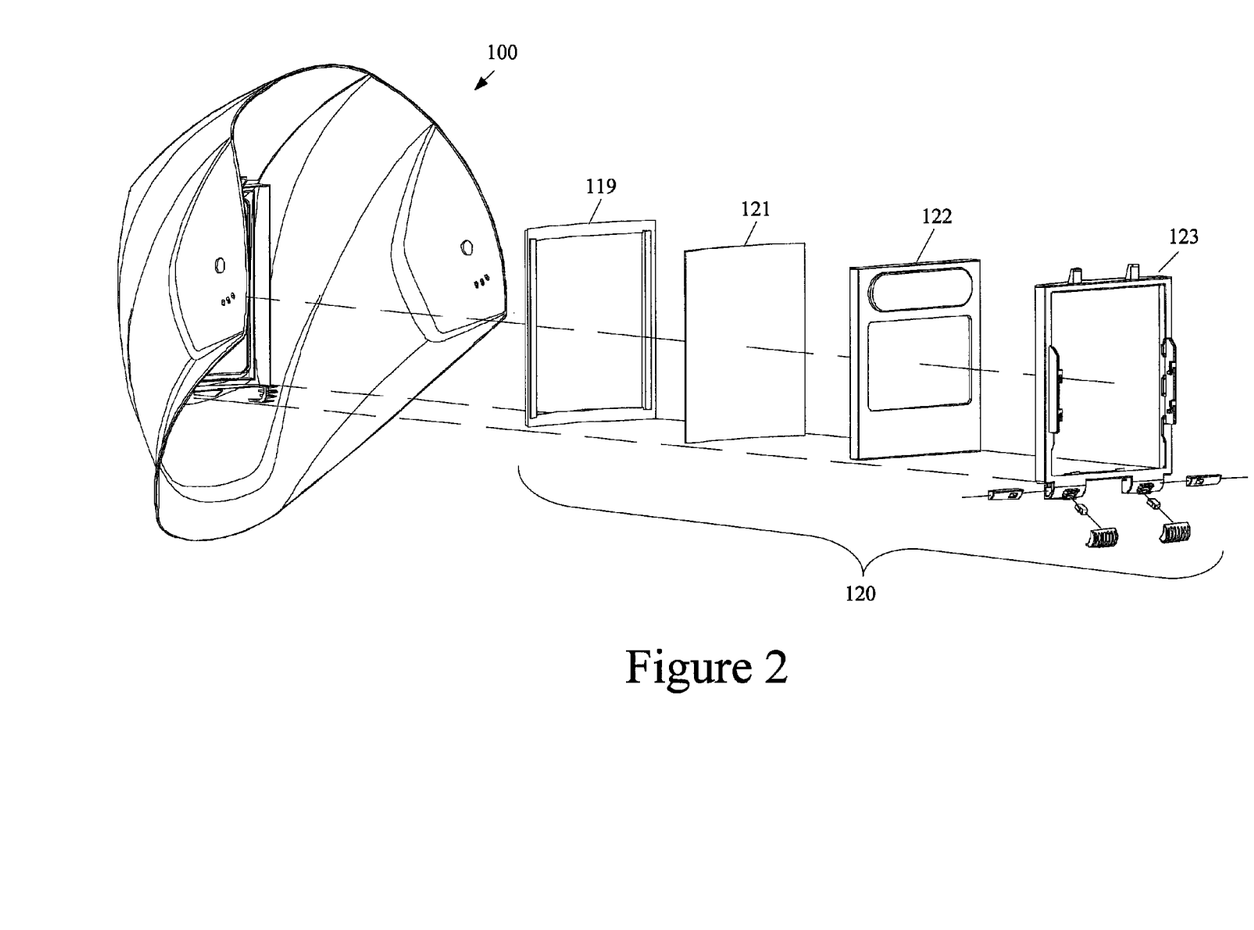
FIG. 2 is an exploded view of the welding mask of FIG. 1.

FIG. 2 shows an exploded view of the welding mask 100. As can be seen in FIG. 2, the observing window 120 generally comprises a frame 119, a protective film 121, an optical filter 122 and a holding system 123. The protective film 121 is mainly configured to protect the optical filter 122 to prolong the life time of the optical filter 122. Because the protective film 121 directly contacts various spatters during welding and is subject to damage, the protective film 121 is typically the only component in the welding mask that needs to be changed regularly. The protective film 121 can be made of transparent materials with high strength, such as glass or plastic. The optical filter 122, which can also be referred to as protective welding glass, is mainly configured to filter out various harmful welding arc lights during the welding operation. An automatic welding filter can be used, which can be switched between a bright state and a dark state so that sufficient light rays are allowed to be passed through in the bright state to make preparations before welding, and the filter is automatically switched to the dark state to filter out harmful rays when welding begins. The optical filter 122 can be generally configured to have a rectangular shape. However, it will be appreciated that the optical filter 122 can have any suitable shape.

The holding system 123 is configured to hold the optical filter 122 and the protective film 121 to the mask casing 110.

The configuration and operation of the holding system 123 will be described in detail below with reference to FIGS. 3A, 3B, 4A, and 4B.

Figures 3A, 3B:
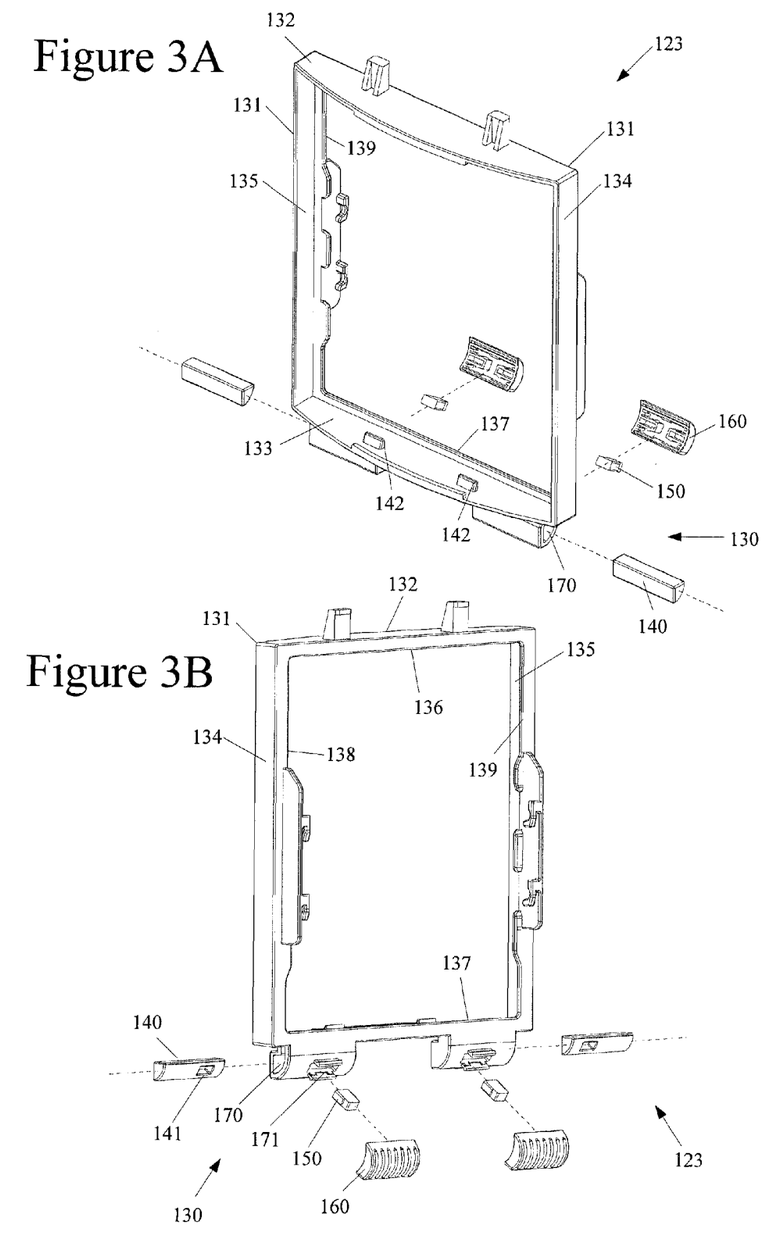
FIGS. 3A and 3B are exploded perspective views of a holding system for the welding mask of FIG. 1.

Referring to FIGS. 3A and 3B, the holding system 123 can include a holding frame body 131 which is configured for holding the optical filter 122 and a connecting mechanism which is configured for connecting the holding frame body 131 to the mask casing 110. The holding system 123, for example, can be made of any suitable material such as nylon. The holding frame body 131 is generally composed of a top wall 132, a bottom wall 133 and two side walls 134, 135 and is configured to be shaped (such as rectangular) in a suitable manner for mating with the shape of the optical filter 122.

Figure 8:
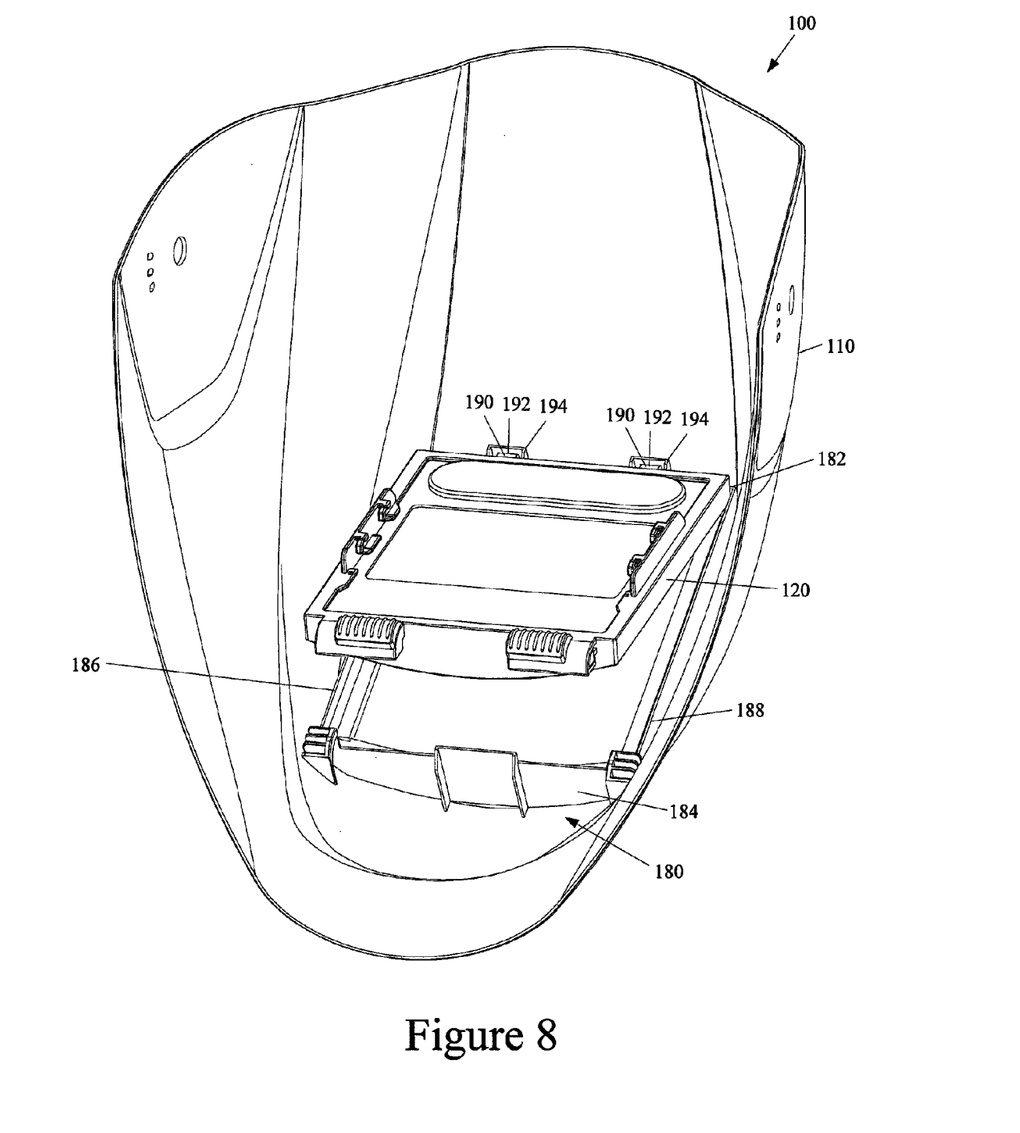
FIG. 8 is a perspective view of the welding mask of FIG. 1, with the holding system in the disconnect position.
Figure 9:
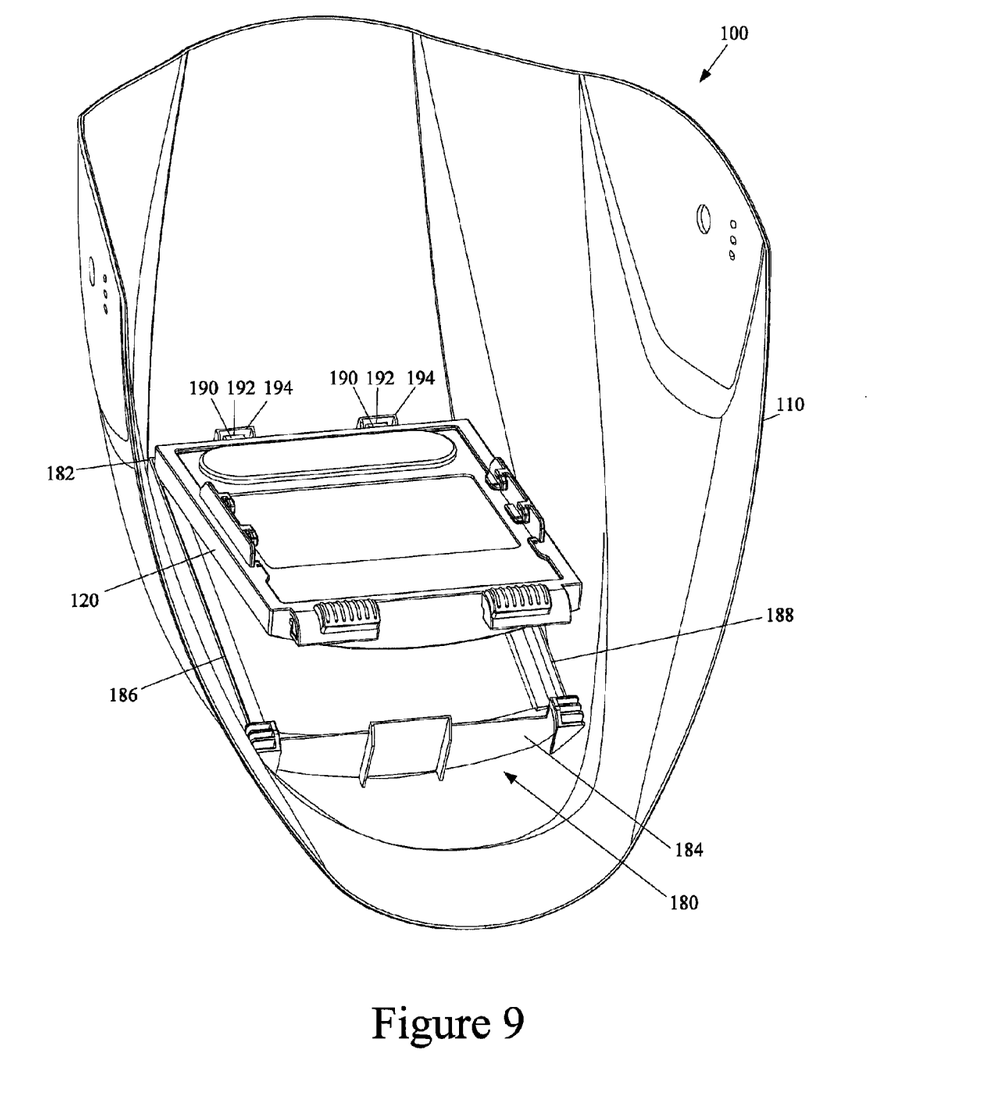
FIG. 9 is a perspective view taken from another angle of the welding mask of FIG. 1, with the holding system in the disconnect position.

Accordingly, as shown in FIGS. 8 and 9, the mask casing 110 is provided with a frame accommodating portion 180, which consists of a top wall 182, a bottom wall 184 and two side walls 186, 188 and is configured for accommodating and supporting the holding system 123. The frame accommodating portion 180 has a shape that is mated with that of the holding frame body 131, so that the top wall 182, the bottom wall 184 and the two side walls 186, 188 of the frame accommodating portion 180 respectively lean against the outside of the top wall 132, the bottom wall 133 and the two side walls 134, 135 of the holding frame body 131 when the holding frame body 131 is placed in the frame accommodating portion 180. The frame accommodating portion 180 can be configured integrally with or fixedly connected to the mask casing. The frame accommodating portion can be made of any suitable material, such as nylon.

In the illustrated embodiment, when the holding frame body 131 is connected to the mask casing 110 via the connecting mechanism, the side of the holding frame body 131 that faces towards an interior space of the mask casing 110 is defined as the inside of the holding frame body 131, while the side of the holding frame body 131 that faces away from the interior space of the mask casing 110 is defined as the outside of the holding frame body 131. For reference purposes, the four directions-top, bottom, left and right-of the holding frame body 131 refer to the orientation of the welding mask 100 when the welding mask 100 is worn on the head of the operator. Unless stated otherwise, the directions as defined above are applied for the description of other components of the welding mask 100.

Referring to FIGS. 3A and 3B, flanges 136, 137, 138, and 139 are provided on the top wall 132, the bottom wall 133, and the two side walls 134, 135, which can be in contact with one another and can have identical thicknesses. The widths of the top wall 132 and the bottom wall 133 of the holding frame body 131 can be larger than the thickness of the optical filter 122, each of the top wall 132 and the bottom wall 133 can be provided with stop protrusions 142. The distances defined by the stop protrusions and the flanges 136, 137 that are provided on the top wall 132 and on the bottom wall 133 respectively can be approximately equal to the thickness of the optical filter 122, so that the optical filter 122 can be positioned between the stop protrusions 142 and the flanges 136, 137, which results in the optical filter 122 being reliably maintained on the holding frame body 131. It will be appreciated that the widths of the two side walls 134, 135 can be slightly larger than the thickness of the filter 122 and one or more stop protrusions can be provided on the two side walls 134, 135, wherein the distance defined by the stop protrusions and the flanges 134, 135 that are provided on the two side walls 134, 135, respectively, are equal to the thickness of the optical filter 122.

According to FIGS. 3A and 3B, the bottom wall 133 of the holding frame body 123 can be provided with connecting mechanisms 130, with a first connecting mechanism provided on the left and a second connecting mechanism on the right. A description of the configuration of the connecting mechanisms will be given first with the first connecting mechanism as an example. The first connecting mechanism 130 can comprise a first connecting pin 140, a first driving block 150 and a first manipulating unit 160.

The first connecting pin 140 can be accommodated in a first connecting pin accommodating cavity 170, which is provided on the bottom wall of the holding frame body 131 and is configured integrally with the holding frame body 131 or is fixedly connected with the holding frame body 131. The first connecting pin accommodating cavity 170 and the first connecting pin 140 can have any suitable cross-sectional shape, such as rectangular, square, or pie-shaped. The first connecting pin 140 can be moved freely in the first connecting pin accommodating cavity 170 leftwards or rightwards. The length of the first connecting pin accommodating cavity 170 can be equal to or greater than that of the first connecting pin 140. In the side wall of the first connecting pin accommodating cavity 170 there can be a through hole 171, which can be rectangular, with the length of the through hole 171 being greater than its width, for example 3-4 times greater than its width. The side wall of the first connecting pin 140 can be provided with a recess 141, which can be rectangular, and the height of the recess 141 can equal the height of the through hole 171 of the first connecting pin accommodating cavity 170, and the length of the recess 141 can be less than the length of the through hole 171 of the first connecting pin accommodating cavity 170, such as approximately by half. When the first connecting pin 140 is accommodated completely in the first connecting pin accommodating cavity 170, the inner wall of the recess 141 of the first connecting pin 140 on the right side can be flush substantially with the inner wall of the rectangular through hole 171 of the first connecting pin accommodating cavity 170 on the right side, while the inner wall of the recess of the first connecting pin 140 on the left side is located approximately centrally in the through hole 171 of the first connecting pin accommodating cavity 170.

Figure 4A:
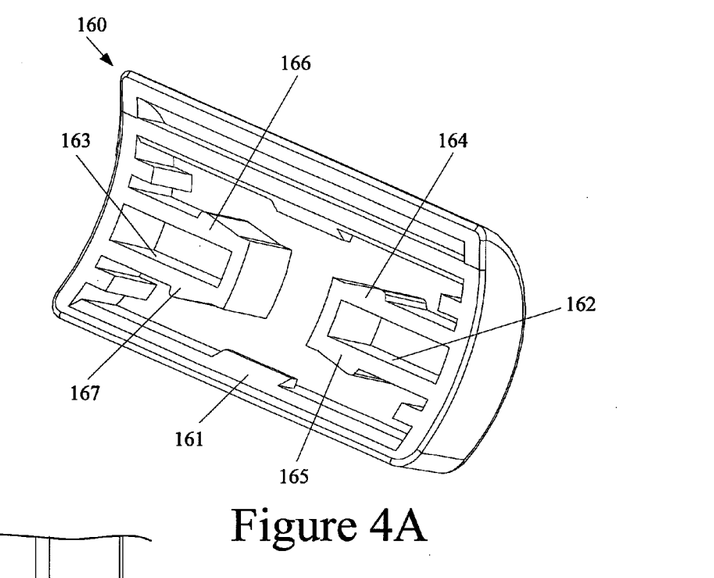
FIG. 4A is an enlarged perspective view of a first manipulating unit for the holding system of FIG. 3A.
Figure 4B:
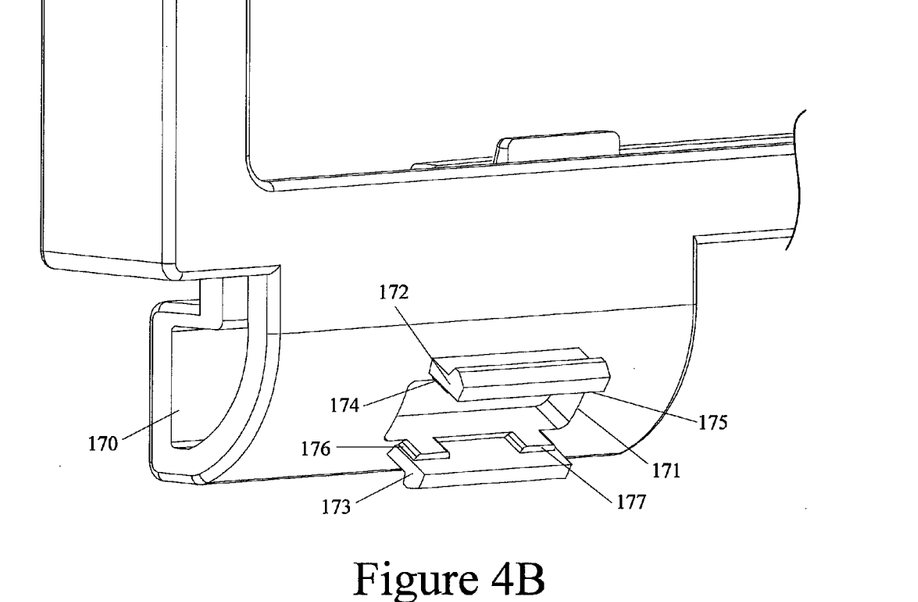
FIG. 4B is an enlarged fragmentary view of the holding system of FIG. 3A.

A partially enlarged view of the holding system is shown in FIGS. 4A and 4B, and more precisely, the first manipulating unit 160 and the first connecting pin accommodating cavity 170 are partially enlarged. The first manipulating unit 160 can be configured for manipulating the first connecting pin 140, so that the latter is switched between a disconnect position and a connect position, wherein in the disconnect position the first connecting pin 140 is completely accommodated in the connecting pin accommodating cavity 170, so that the holding frame body 131 can be separated from the mask casing 110, and wherein in the connect position the first connecting pin 140 extends laterally out of the first connecting pin accommodating cavity 170 and is inserted into a corresponding accommodating cavity provided on the mask casing 110, which results in the holding frame body 131 being reliably connected to the mask casing 110.

In order to manipulate the first connecting pin 140, the first manipulating unit 160 should be able to be moved leftwards or rightwards under a manipulating force. To this end, on the side wall of the first connecting pin accommodating cavity 170, rails 172, 173 are provided respectively above and below the through hole 171, wherein the upper rail 172 is formed by a protrusion which extends from the side wall of the first connecting pin accommodating cavity 170 and which is provided with an upwardly protruding flange on the outer edge, while the lower rail 173 is formed by a protrusion which extends from the side wall of the first connecting pin accommodating cavity 170 and which is provided with a downwardly protruding flange on the outer edge. The lengths of the rails 172, 173 can be slightly smaller than that of the through hole 171 of the first connecting pin accommodating cavity 170.

Guiding protrusions 161 can be provided inside of the top wall and of the bottom wall of the first manipulating unit 160 respectively, and each can be disposed in the middle of the top wall and the bottom wall. The flanges of the rails 172, 173 and the guiding protrusions 161 of the first manipulating unit 160 can be made of elastic materials. The first manipulating unit 160 can be placed on the rails 172, 173 by means of an external force, so that the inner end surface of the guiding protrusions 161 of the first manipulating unit 160 and the inner end surface of the flanges of the rails 172, 173 come into contact with each other such that the first manipulating unit 160 can slide leftwards or rightwards. A first stop protrusion 174 and a second stop protrusion 175 can be located on the bottom side of the upper rail 172. The first stop protrusion 174 can be provided on the left side of the rail 172, and the second stop protrusion 175 can be provided on the right side of the rail 172.

Similarly, a third stop protrusion 176 and a fourth stop protrusion 177 can be located on the top side of the lower rail 173, wherein the third stop protrusion 176 is provided on the left side of the rail 173, and the fourth stop protrusion 177 is provided on the right side of the rail 173.

The side walls of the first manipulating unit 160 can have a first positioning unit 162 and a second positioning unit 163. The heights of the two positioning units 162, 163 correspond to the distance between the upper rail 172 and the lower rail 173, so that the first positioning unit 162 and the second positioning unit 163 can be moved leftwards or rightwards between the upper rail 172 and the lower rail 173 when the first manipulating unit 160 is placed on the rails 172, 173. The first positioning unit 162 and the second positioning unit 163 are separated from one another, and the distance between the first positioning unit 162 and the second positioning unit 163 can approximately equal the length of the recess 141 of the first connecting pin 140. A first positioning protrusion 164 can be provided on the top wall and a second positioning protrusion 165 can be provided on the bottom wall of the first positioning unit 162. The first positioning protrusion 164 and second positioning protrusion 165 are on the end of the first positioning unit 162 that is away from the side wall of the first manipulating unit 160. Similarly, a third positioning protrusion 166 can be provided on the top wall and a fourth positioning protrusion 167 can be provided on the bottom wall of the second positioning unit 163. The third positioning protrusion 166 and fourth positioning protrusion 167 can be located on the end of the second positioning unit 163 that is away from the side wall of the first manipulating unit 160.

Referring to FIGS. 3A and 3B, the first driving block 150 is configured to connect the first connecting pin 140 with the first manipulating unit 160, so that the first connecting pin 140 can be moved leftwards or rightwards with the first manipulating unit 160. An end of the first driving block 150 is situated in the rectangular recess 141 of the first connecting pin, while the other end of the first driving block 150 is situated in the manipulating unit 160 in the gap between the first positioning unit 162 and the second positioning unit 163.

With the first connecting mechanism as an example, and with reference to FIGS. 3A-7, a description will be given with regard to the working principle of the connecting mechanisms 130.

Figure 5A:
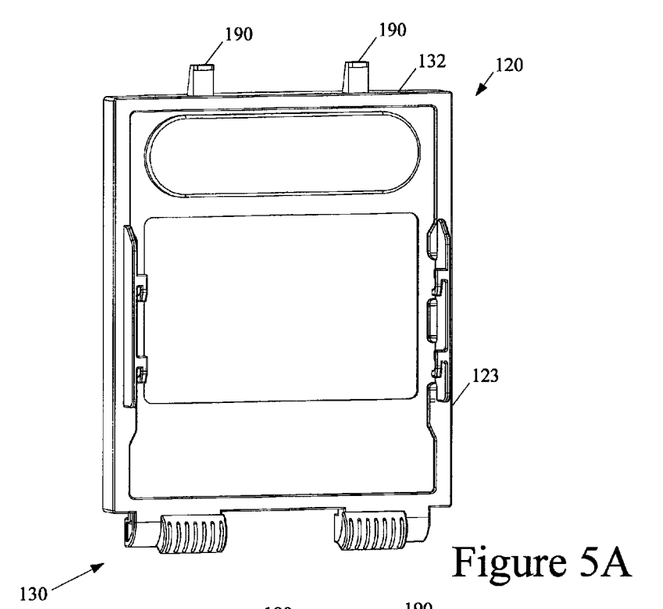
FIGS. 5A and 5B are perspective views of the holding system of FIG. 3A, with the holding system in a disconnect position and in a connect position respectively.
Figure 6:
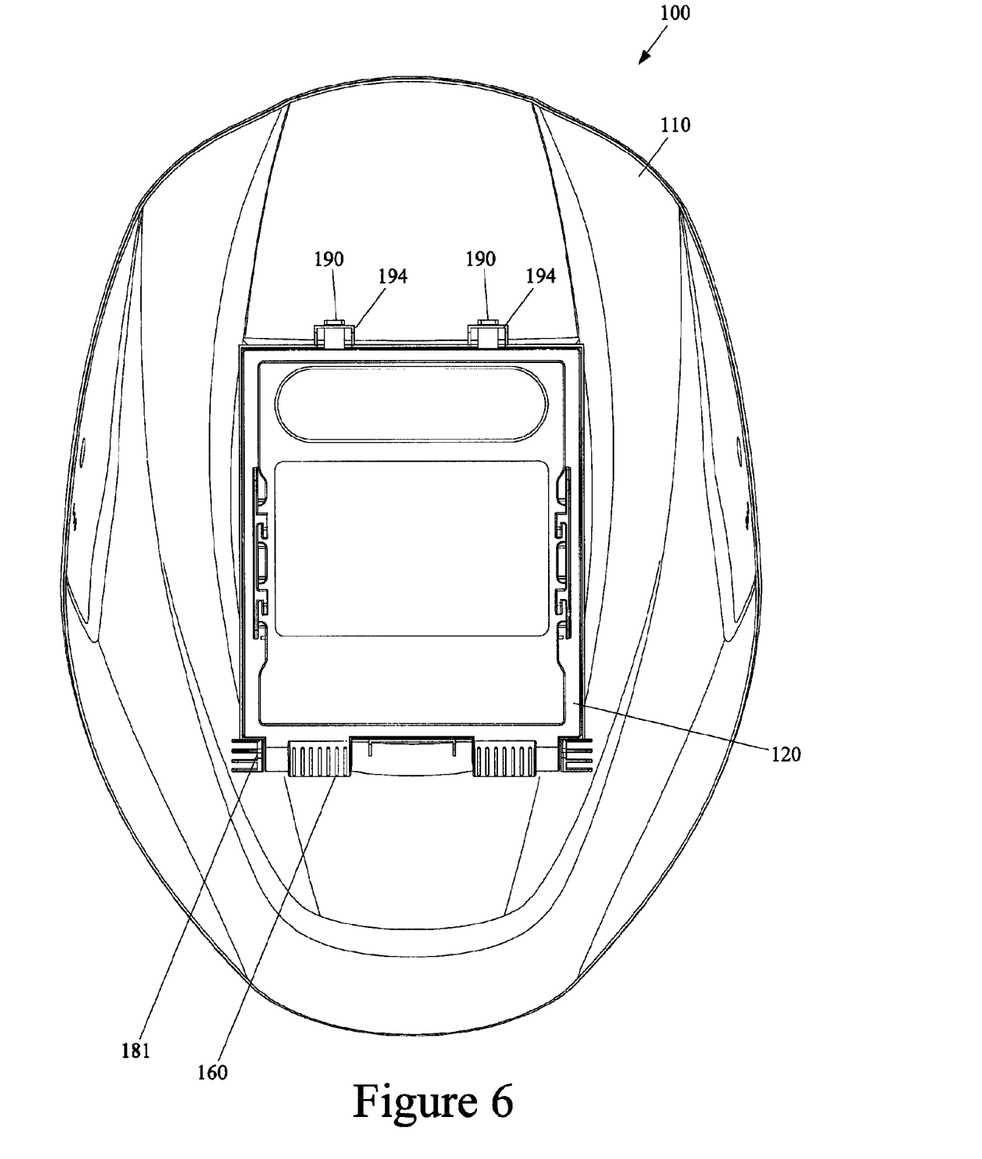
FIG. 6 is an elevational view of the welding mask of FIG. 1, with the holding system in the disconnect position.

In a disconnect position of the connecting mechanism, the first stop protrusion 174 of the rail 172 is situated between the first positioning protrusion 164 of the first manipulating unit 160 and the side wall of the first manipulating unit 160 on which the first positioning unit 162 is located (or the end surface of a protrusion that extends from the side wall of the first manipulating unit). The third stop protrusion 176 of the rail 173 is situated between the second positioning protrusion 165 of the first manipulating unit 160 and the side wall of the first manipulating unit 160 on which the first positioning unit 162 is located (or the end surface of a protrusion that extends from the side wall of the first manipulating unit). In addition, the second stop protrusion 175 of the rail 172 and the fourth stop protrusion 177 of the rail 173 are situated substantially in the gap between the first positioning unit 162 of the first manipulating unit 160 and the second positioning unit 163, so that in the disconnect position the first connecting pin 140 is completely accommodated in the first connecting pin accommodating cavity 170 by means of the first driving block 150 as shown in FIGS. 5A and 6.

Figure 5B:
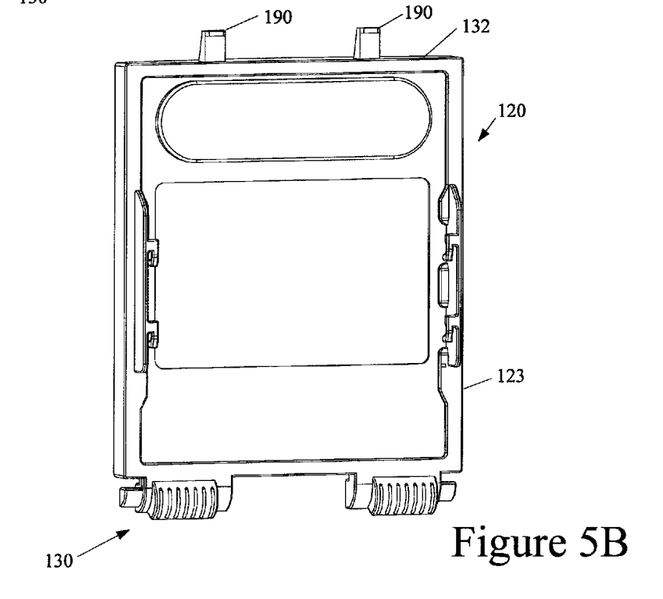
Figure 7:
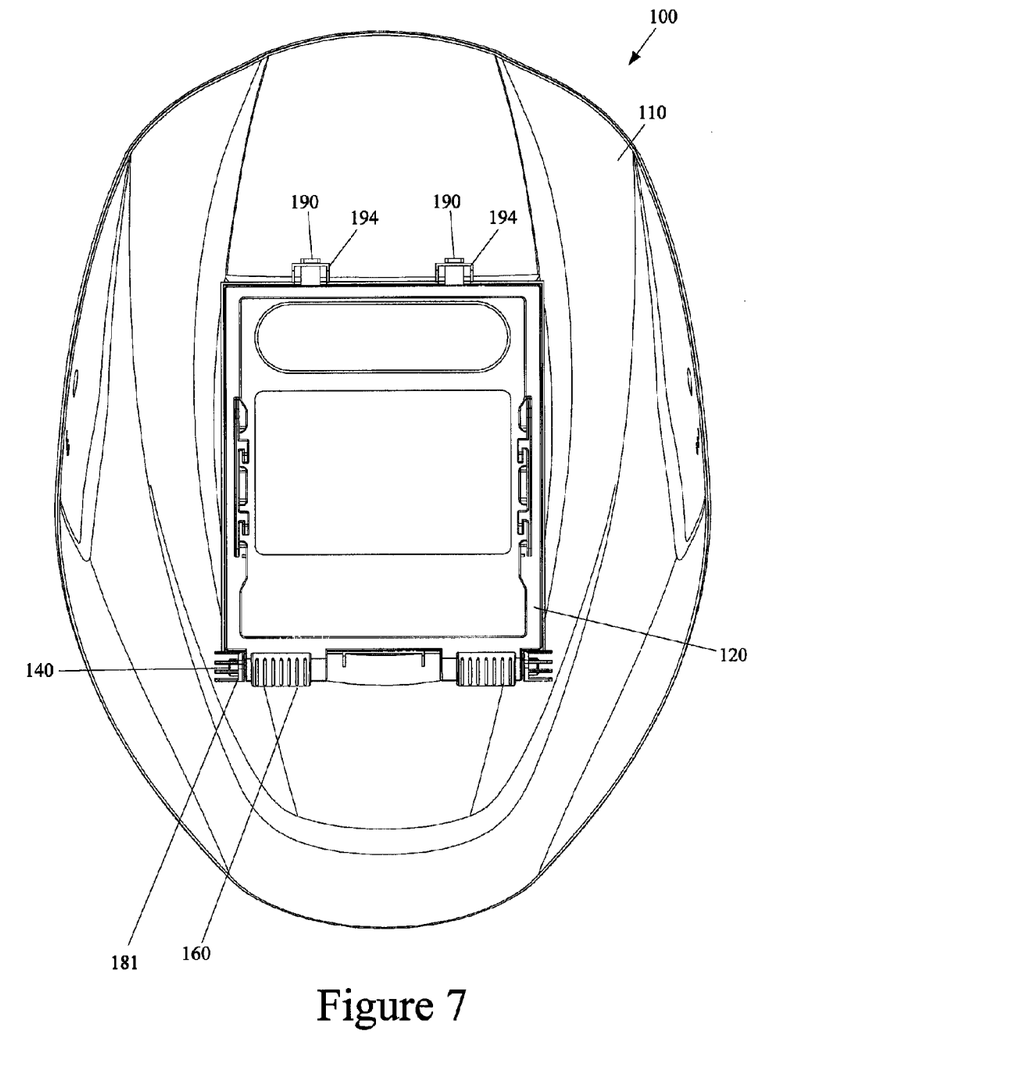
FIG. 7 is an elevational view of the welding mask of FIG. 1, with the holding system in the connect position.

In a connect position of the connecting mechanism, the third stop protrusion 175 of the rail 172 is situated between the third positioning protrusion 166 of the first manipulating unit 160 and the side wall of the first manipulating unit 160 on which the second positioning unit 163 is located (or the end surface of a protrusion that extends from the side wall of the first manipulating unit), and the fourth stop protrusion 177 of the rail 173 is between the fourth positioning unit 167 of the first manipulating unit 160 and the side wall of the first manipulating unit 160 on which the second positioning unit 163 is located (or the end surface of a protrusion that extends from the side wall of the first manipulating unit). In addition, the first stop protrusion 174 of the rail 172 and the third stop protrusion 174 of the rail 173 are situated substantially in the gap between the first positioning unit 162 of the first manipulating unit 160 and the second positioning unit 163, so that in the connect position the first connecting pin 140 extends leftwards out of the first connecting pin accommodating cavity 170 as shown in FIG. 5B and is inserted into the corresponding accommodating cavity 181 provided on the mask casing as shown in FIG. 7.

The second connecting mechanism can have substantially the same configuration and operation as the first connecting mechanism, wherein in the connect position, a second connecting pin of the second connecting mechanism extends rightwards out of a second connecting pin accommodating cavity and is inserted into an accommodating cavity provided on the mask casing.

The top wall of the holding frame body can also include a third connecting mechanism and a fourth connecting mechanism. The third connecting mechanism and the fourth connecting mechanism each can have the same configuration and operation as the first connecting mechanism or the second connecting mechanism. In the connect position, the first connecting mechanism and the third connecting mechanism can be connected with the mask casing on the left via respective connecting pins, while the second connecting mechanism and the fourth connecting mechanism can be connected with the mask casing on the right via respective connecting pins.

In an alternative embodiment, as shown in FIGS. 5A-9, rather than using the third connecting mechanism and the fourth connecting mechanism, protrusions 190 can be provided on the top wall 132 of the holding frame body 131, which can be inserted into through holes 192 of mounting brackets 194 provided on the mask casing 110, so that the holding frame system 123 can be stopped in a front and back direction in the connected position. Similarly, in another embodiment, if the third connecting mechanism and the fourth connecting mechanism are on the top wall, then instead of the first connecting mechanism and the second connecting mechanism, on the bottom wall of the holding frame body 133, there can be on or more protrusions that can cause the holding frame to be stopped in the front and back direction in the connected position.

In order to facilitate the transition between the disconnect position and the connect position, the first positioning protrusion 164, the second positioning protrusion 165, the third positioning protrusion 166 and the fourth positioning protrusion 167 of an individual manipulating unit 160 can be configured to have a wedge shape, and wherein the face that is away from the side wall of the manipulating unit 160 is configured to be a gentle incline.

The outer surface of the manipulating unit 160 can be roughened. The roughness of the outer surface of the manipulating unit 160 can be achieved with a plurality of ribs that extend along a direction that is perpendicular to the moving direction and that protrude from the outer surface of the manipulating unit 160. The roughened outer surface of the manipulating unit facilitates movement of the manipulating unit leftwards and rightwards by the operator. In the longitudinal section, the manipulating unit 160 can have any suitably shape.

Different states of the holding system are shown in FIGS. 5A and 5B. FIG. 5A shows the connecting mechanism 130 in the disconnect position, wherein the connecting pin 140 is completely accommodated in the connecting pin accommodating cavity 170, and FIG. 5B shows the connecting mechanism 130 in the connect position, wherein the connecting pin 140 extends laterally out of the connecting pin accommodating cavity 170 to connect with the mask casing 110.

FIGS. 6 and 7 show the observing window 120 with the welding mask 100. As shown, the connecting mechanism 130 of the welding mask 100 in FIG. 6 is in the disconnect position, and the connecting mechanism 130 of the welding mask 100 in FIG. 7 is in the connect position.

FIGS. 8 and 9 show, from different angles, the connecting mechanism 130 in the disconnect position and show how the observing window 120 can be separated or attached to the welding mask 100 by conveniently pivoting the observing window into and out of place without the use of any tools.

The observing window 120 can be attached to the mask casing using the above-mentioned connecting mechanism 130 through the following steps:

Firstly, placing the protective film in the frame accommodating portion provided on the mask casing.

Next, fixing the filter on the holding frame body, and then placing the holding system with the filter in the frame accommodating portion of the mask casing. The protrusions on the holding system can be mated into the respective through holes on the mask casing.

Finally, the manipulating unit of the holding system can be moved to cause the connecting pin of the holding system to be inserted into the corresponding accommodating cavity provided on the mask casing so that the protective film and the filter are maintained on the mask casing simultaneously.

Although the filter holding system is described and explained with regard to specific embodiments, the invention is not intended to be limited to the described details. Various modifications on the details can be made without departing from the claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A filter holding system for holding an optical filter to a mask casing of a welding mask, the filter holding system comprising:
   a holding frame body configured to support and accommodate the optical filter; and
   a connecting mechanism provided on the holding frame body, the connecting mechanism being configured to connect and disconnect the holding frame body to and from the mask casing,
   wherein the connecting mechanism is moveable between a disconnect position and a connect position;
   wherein, when at the disconnect position, the connecting mechanism disconnects the holding frame body from the mask casing such that the holding frame body and the mask casing are separable from each other;
   wherein, when at the connect position, the connecting mechanism connects the holding frame body to the mask casing;
   wherein the connecting mechanism further comprises a connecting pin and a manipulating unit;
   wherein the connecting pin is accommodated in a connecting pin accommodating cavity of the holding frame body;
   wherein, when at the connect position, the connecting pin extends laterally out of the connecting pin accommodating cavity of the holding frame body such that the connecting pin is adapted to be disposed in an accommodating cavity of the mask casing and wherein, when at the disconnect position, the connecting pin does not extend laterally out of the connecting pin accommodating cavity of the holding frame body, such that at the disconnect position the connecting pin is not adapted to be disposed in the accommodating cavity of the mask casing;
   wherein the manipulating unit is connected to the connecting pin such that movement of the manipulating unit is configured to switch the connecting pin between the disconnect position and the connect position; and
   wherein a plurality of rails are provided on a side wall of the connecting pin accommodating cavity of the holding frame body, and the manipulating unit is disposed on the holding frame body such that the manipulating unit is slidable along the rails.

2. The filter holding system according to claim 1, wherein the connecting mechanism further comprises a driving block;
   wherein the driving block is secured at an end through a hole of the frame body to a recess of the connecting pin, with the manipulating unit receiving a second end of the driving block.

3. The filter holding system according to claim 1, wherein a plurality of stop protrusions are provided on the rails, a plurality of corresponding stop protrusions are provided on the manipulating unit, and the manipulating unit is configured to be positioned in the disconnect position and in the connect position by mating the stop protrusions of the rails with the corresponding stop protrusions of the manipulating unit; and
   wherein the manipulating unit is switchable between the disconnect position and the connect position by asserting an external force on the manipulating unit.

4. The filter holding system according to claim 1, further comprising a second connecting mechanism, wherein the connecting mechanisms are disposed on a bottom wall of the holding frame body, and wherein one or more protrusions are disposed on a top wall of the holding frame body which are configured to pass through one or more through holes provided on the mask casing.

5. The filter holding system according to claim 1, wherein the connecting mechanism is disposed on at least one of a bottom wall and a top wall of the holding frame body, and a second connecting mechanism is disposed on at least the other one of the bottom wall and the top wall of the holding frame body.

6. The filter holding system according to claim 1, wherein an outer surface of the manipulating unit is roughened.

7. The filter holding system according to claim 1, wherein the holding system is made of synthetic fiber.

8. A welding mask, comprising: a mask casing, a protective film, a headgear, an optical filter and a filter holding system;
   wherein the optical filter is held in the filter holding system and is connected on the welding mask with the filter holding system;
   wherein the filter holding system comprises:
      a holding frame body configured to support and accommodate the optical filter; and
      a connecting mechanism provided on the holding frame body, the connecting mechanism being configured to connect and disconnect the holding frame body to and from the mask casing;
   wherein the connecting mechanism is moveable between a disconnect position and a connect position;
   wherein, when at the disconnect position, the connecting mechanism disconnects the holding frame body from the mask casing such that the holding frame body and the mask casing are separable from each other;

wherein, when at the connect position, the connecting mechanism connects the holding frame body to the mask casing;

wherein the connecting mechanism further comprises a connecting pin and a manipulating unit;

wherein the connecting pin is accommodated in a connecting pin accommodating cavity of the holding frame body;

wherein, when at the connect position, the connecting pin extends laterally out of the connecting pin accommodating cavity of the holding frame body such that the connecting pin is inserted into an accommodating cavity of the mask casing and wherein, when at the disconnect position, the connecting pin does not extend laterally out of the connecting pin accommodating cavity of the holding frame body, such that at the disconnect position the connecting pin is not inserted into the accommodating cavity of the mask casing; and wherein the manipulating unit is connected to the connecting pin such that movement of the manipulating unit is configured to switch the connecting pin between the disconnect position and the connect position.

9. The welding mask according to claim 8, wherein the connecting mechanism further comprises a driving block;

wherein the driving block is secured at an end through a hole of the frame body to a recess of the connecting pin, with the manipulating unit receiving a second end of the driving block.

10. The welding mask according to claim 8, wherein a plurality of rails are provided on a side wall of the connecting pin accommodating cavity of the holding frame body, and the manipulating unit is disposed on the holding frame body such that the manipulating unit is slidable along the rails.

11. The welding mask according to claim 10, wherein a plurality of stop protrusions are provided on the rails, a plurality of corresponding stop protrusions are provided on the manipulating unit, and the manipulating unit is configured to be positioned in the disconnect position and in the connect position by mating the stop protrusions of the rails with the corresponding stop protrusions of the manipulating unit; and wherein the manipulating unit is switchable between the disconnect position and the connect position by asserting an external force on the manipulating unit.

12. The welding mask according to claim 8, further comprising a second connecting mechanism, wherein the connecting mechanisms are disposed on a bottom wall of the holding frame body, and wherein one or more protrusions are disposed on a top wall of the holding frame body which are configured to pass through one or more through holes provided on the mask casing.

13. The welding mask according to claim 8, wherein the connecting mechanism is disposed on at least one of a bottom wall and a top wall of the holding frame body, and a second connecting mechanism is disposed on at least the other one of the bottom wall and the top wall of the holding frame body.

14. The welding mask according to claim 8, wherein an outer surface of the manipulating unit is roughened.

15. The welding mask according to claim 8, wherein the holding system is made of synthetic fiber.

* * * * *